(12) United States Patent
Tondar et al.

(10) Patent No.: US 6,383,553 B1
(45) Date of Patent: May 7, 2002

(54) METHOD FOR MONITORING AND/OR CONTROLLING A GRANULATION, COATING AND DRYING PROCESS

(75) Inventors: Mathias Tondar, Hausen; Bernhard Luy; Armin Prasch, both of Freiburg, all of (DE)

(73) Assignee: Glatt GmbH, Binzen (DE)

( * ) Notice: Subject to any disclaimer, the term of this patent is extended or adjusted under 35 U.S.C. 154(b) by 0 days.

(21) Appl. No.: 09/405,201

(22) Filed: Sep. 24, 1999

Related U.S. Application Data

(63) Continuation of application No. PCT/EP98/01629, filed on Mar. 20, 1998.

(30) Foreign Application Priority Data

Mar. 27, 1997 (DE) .......................................... 297 05 574
Jun. 6, 1997 (DE) .......................................... 197 23 995

(51) Int. Cl.[7] .............................. B05D 1/22; C22B 1/14
(52) U.S. Cl. ........................... 427/8; 427/185; 427/459; 23/313 FB; 34/474
(58) Field of Search ........................... 427/8, 459, 185; 118/309, 688; 23/313 R, 313 FB; 34/528, 445, 446, 474

(56) References Cited

U.S. PATENT DOCUMENTS 4,698,190 A * 10/1987 Shibata et al.
5,459,318 A * 10/1995 Cache et al.
5,497,232 A * 3/1996 Watano et al.

FOREIGN PATENT DOCUMENTS

| DE | 40 14 915 A1 | 11/1991 |
| DE | 44 28 978 A1 | 3/1995 |
| EP | 0 249 738 A1 | 12/1987 |
| EP | 0 403 820 A1 | 12/1990 |
| EP | 0 403 820 | * 12/1990 |

OTHER PUBLICATIONS

T. Hauschild, et al., "Density Monitoring In Circulating Fluidized Beds Using A Microwave Sensor", *Proceedings of The 23RD European Microwave Conference*, Sep. 6, 1993, European Microwave Conference Management Committee, pp. 260–263 (XP000629927).

* cited by examiner

*Primary Examiner*—Fred J. Parker
(74) *Attorney, Agent, or Firm*—Akin, Gump, Strauss, Hauer & Feld, L.L.P.

(57) ABSTRACT

A method and a device function for monitoring and/or controlling and regulating a granulation, agglomeration, instantization, coating and drying process in a fluidized layer or a moving bulk by determining the product moisture. At least during one process segment the total product moisture is measured substantially continuously over a period of seconds, in a contact-free manner using electromagnetic radiation in the high frequency or microwave range, by evaluation of the attenuation of the radiation as a measure of this total product moisture. Taking into account the product temperature, the measurement result is used to hold the total product moisture in a pre-determined range via a control circuit by changing the spray rate and/or the gas temperature and/or the volume flow.

6 Claims, 2 Drawing Sheets

METHOD FOR MONITORING AND/OR CONTROLLING A GRANULATION, COATING AND DRYING PROCESS

CROSS REFERENCE TO RELATED APPLICATION

This application is a continuation of International Application PCT/EP98/01629, filed Mar. 20, 1998, the disclosure of which is incorporated herein by reference.

BACKGROUND OF THE INVENTION

The invention relates to a method and a device for monitoring and/or controlling and regulating a granulation, agglomeration, instantization, coating and/or drying process in a fluidized bed or a moving bulk by determining the product moisture.

In the prior art indirect methods are known for determining the product moisture, for example using a balancing of the inlet and outlet streams from which the product moisture is determined. The inlet and exhaust air conditions (temperature and humidity) are measured, as well as the volume flow of the inlet and exhaust air and the spray rate. From many different measuring positions (a minimum of seven measurement quantities), a correspondingly large number of measurement errors results and thereby a product moisture that is not exactly specified. Problems occur especially for processes which require a fast regulation, for example the detection of the shut-off point for spraying during granulation. An indirect measurement of the humidity of the product environment can be performed by a capacitive measuring sensor which is positioned directly in the fluidized bed. Generally, the actual measurement sensor is surrounded by a water vapor-permeable protection cap, through which the water vapor must diffuse, which is then correspondingly detected by the sensor.

It is problematic therein that this involves a slow measuring method. During granulation, an air atmosphere always appears in the product environment which is almost completely saturated with water, which can lead to condensation on the sensor (so-called over-moistening of the sensor). The condensed water requires a considerably longer time until it is released again to the outside via the protection cap. During this time, the measurement signal always lies at about 100% air humidity. Furthermore, contamination of the sensor can lead to considerable measurement error. In addition, as a result of the partly strong abrasive forces by the fluidized product, the sensor only has a short service life.

Using NIR-spectroscopy, only the surface moisture can be measured. Usually, a very high calibration expense and an expensive mathematical evaluation and averaging of the measurement signal are necessary for this. The IR-sensor can be integrated in the fluidized layer only via a window that is flush with the wall, so that problems result from glazing of the window, because this leads to the immediate reflection of radiation. A measurement is then ruled out. Furthermore, due to the short wavelengths and the high reflection of the radiation thus present, there is no penetration depth into the fluidized layer or the product. Thus, only the surface moisture can be recorded. Finally, the dependence of the measurement signal on the grain size and on the bulk density, and the dependence of the measurement signal on the color change and the thereby resulting high calibration expense, are disadvantageous.

A measurement of the moisture can also be performed via an impedance measurement with two electrodes on an electrically insulating substrate (PTFE), which are connected together to be electrically conducting via a moisture-sensitive layer of an electrolytic solid (water vapor permeable). An equilibrium humidity is measured, which appears in the product environment. The direct product moisture is not measured. The service life of the sensor in the fluidized layer is very unsatisfactory.

Furthermore, it is known to record the levels of inlet and exhaust air temperature, volume flow, inlet and exhaust air humidity, and the spray rate. From these quantities, however, generally only indirect information can be derived about the actual product or the water content appearing in the product. Exact readings are generally only possible with off-line measurement methods, such as dry weight determination, vacuum drying chamber, desiccator method, infrared scales, or by the Karl-Fischer titration. These methods are, however, very time consuming and require a time expenditure of 10 minutes to half a day for a moisture measurement, so that these methods permit no real-time or current information for the process.

A further possibility for detecting the result or the progression of a granulation process is represented by the possibility of directly determining or measuring the particle size or the grain size distribution during the process. The processes known for this, such as ultrasound measurement or laser diffraction spectroscopy, are characterized by a very high cost of devices and by extremely complicated mathematical and statistical evaluation procedures. For the measurement, defined measurement sections, for example a defined bypass for the product, are usually necessary, such that an insertion directly into the fluidized layer is not possible. A reproducibility of the method is generally achieved only under certain conditions.

With all of the above-mentioned known processes for controlling or regulating the processes, it is disadvantageous that they are either too slow and/or too susceptible to disturbances and/or not accurate enough, and therefore a limited practical suitability is available only for certain products.

SUMMARY OF THE INVENTION

An object of the present invention is to create a method of the type mentioned at the beginning, as well as a device, whereby under the more difficult conditions that are prevalent with these processes, in particular with respect to the accessibility of the product, the contamination and the service life of the sensor, etc., the product moisture can be measured reliably with higher measurement accuracy, and this measurement quantity can be used for the control or the regulation of the process. In particular, this moisture measurement should provide a result that can be used directly as a measure for certain product characteristics. Moreover, the measurement should also be applicable for different products without costly adaptation and calibration.

In order to achieve this object, it is proposed that, at least during one segment of the process, the total product moisture is measured substantially continuously at least over a period of seconds, in a contact-free manner using electromagnetic radiation in the high frequency or microwave range, by evaluation of the attenuation as a measure of this total product moisture, and taking into consideration the product temperature, the total product moisture is held in a pre-determined range via a control circuit by changing the spray rate and/or the gas temperature and/or the volume flow.

The invention is based upon the discovery that the total product moisture, and consequently both the surface moisture as well as the moisture present within the product in the capillaries or the cavities of a granulate grain, is a key piece of information, by which an exact influence of the respective process is possible.

From European published patent application EP-A-0 403 820 a process for drying a bulk is indeed known, in which an electromagnetic radiation is used in order to dry the bulk and to measure its moisture. The electromagnetic radiation is used therein for drying the bulk, wherein the microwave device functions as an active drying device, while the reflected output is only measured in order to determine the end of the drying process. However, no indication is contained therein that the electromagnetic radiation is used only for measurement and that this measurement is used to control the total product moisture by adjustment of the spray rate.

The method according to the invention and the corresponding measurement device constitute an improvement of a conventional process, in which the drying is not influenced by the microwave radiation, so that measurement data are available about the actual, directly present total product moisture, which can thus be used directly, i.e., "online", as process-accompanying measurement quantities for the control of the directly on-going process. The device according to the invention makes it possible to measure the product moisture within very narrow limits, exactly and reproducibly. By the continuous on-line detection of the product moisture, one obtains, for example during a granulation process, a reproducible grain size distribution wherein the total product moisture is practically a direct measure for the grain size distribution.

The following embodiments make clear the interdependence between the total product moisture and certain product characteristics.

Via the interfacial forces and the capillary pressure on freely moving liquid surfaces, the necessary cohesion occurs between the product grains for the granulate formation from several grains. A distinction must be made therein whether the cavities between the individual grains are filled with liquid only partially (formation of liquid bridges between the grains) or completely (formation of capillary adhesive forces). Likewise, several solid grains can be surrounded by a complete liquid skin, whereby surface tension forces can lead to an agglomeration of several drops. As a result of these mechanisms, with moist granulation there occurs both a defined grain enlargement and a defined reduction of already existing granulates. Besides product-specific properties, such as wettability, porosity and hygroscopicity, a significant influence on the granulation results from the absolute content of product moisture. The product moisture results from the adjusted spray rate and the drying output in the course of the granulation (between the particle sizes, the spray rate and the particle grain).

For the size growth rate, and thus also for the grain size distribution of the granulation, the following functional relationship exists for a moist granulation essentially via the particle surface available for the exchange:

The granulation occurs through adherence of particles, not yet been granulated or less strongly granulated, on the still moist particle surface of other, mostly larger particles. The larger the particle surface relative to volume (i.e., the smaller the particles), the larger the drying capacity. The larger the particles, the smaller the particle surface relative to volume and thus the smaller the drying capacity. Toward the end of the granulation an over-moistening of the product can easily occur in the case of a constant spray rate, which can lead to uncontrolled agglomeration and process interruption. The total product moisture thus represents a significant parameter for controlling and regulating a granulation process. Because of the relationship shown, a reproducible granulation mechanism results. The product moisture is accordingly a direct measurement. The product-related result can be characterized by the grain size distribution.

There is also the possibility that, via the measurement of the total product moisture in a granulation/coating process, the maximum permissible product moisture is determined for maintaining a stable and homogeneous fluidization, and/or a pre-determinable, constant product moisture is regulated and/or the end point of the granulation is determined.

Furthermore, the possibility exists that, via the measurement of the total product moisture during a drying process, the end of the process is determined during drying at a desired end moisture content. This possibility is particularly usable when the drying represents the last phase of a granulation process for reaching a pre-determined end moisture.

Finally, by the measurement of the total product moisture, a pre-determinable moisture progression can be regulated via a direct correlation between the spray rate and the product moisture.

Special advantages also result in use in the context of the so-called "scale-up." In this regard, for a calibration in the context of a process adjusted to the laboratory standard, and the adaptation of the process based thereupon to an actual production standard, the adjustment of the spray rate exclusively via the measurement of the total product moisture is performed as a quantity that is not a function of the instruments. In particular, during this scale-up, an instrument-independent quantity is available with the total product moisture measured using electromagnetic radiation, which quantity as a measure makes possible the transfer of process conditions from small scale to large scale.

The invention also relates to an aeration device, in particular a fluidized layer apparatus with a container and an impermeable seal, which has a sealing part insertable in a container wall opening, wherein for the process control a control circuit is provided at least with one temperature sensor as well as mechanisms for changing the spray rate and/or the gas temperature and/or the volume flow.

This device is characterized in that in the impermeable seal, a microwave sensor is integrated as a moisture sensor, which is connected via an electric cable to an evaluation device as part of the process control, that the impermeable seal has a sensor holder formed by a carrier member, and that the carrier member or the moisture sensor is arranged for a seal to the container wall that is approximately flush with the inner wall and is free of dead spaces.

With an aeration device of this type the method can be performed especially well, because when using a microwave sensor, among other things, special sampling devices having direct access into the fluidized bed or coverings are not necessary.

The use of the microwave sensor in connection with the impermeable seal in a dead space-free arrangement has the essential advantage that the system and the components used—impermeable seals, sensors—can be easily cleaned, which is also possible when the system is closed. In connection with the provided impermeable seal, the sensor can still be retrofit in a simple manner later.

It is also advantageous that the microwave sensor installed in the impermeable seal is connected only via a cable as the control line to the evaluation device. The length of the cable therefore plays practically no role, so that the evaluation device connected thereto can be arranged set apart from the fluidized layer apparatus. This is a considerable advantage, because in the area surrounding the fluidized layer there is often little space available, and because the devices arranged in this direct production area must be cleaned according to exactly prescribed steps, which in the present case is not applicable.

Expediently, the carrier member has a recess for receiving the microwave sensor and is preferably constructed as a protection cap for the sensor. The cap is preferably made of polytetrafluoroethylene (PTFE) and closes off the container inner wall in an approximately flush manner. The sensor is thereby housed in a well-protected manner, and by the carrier member that seals in a flush manner with the container interior, the container inner wall is continued in an approximately continuous manner, without disruptive parts projecting into the container interior. In order to be able to replace the microwave sensor easily, when necessary, a detachable cover flange is provided for the detachable mounting of the microwave sensor. The sensor, which can be constructed, for example, as a planar sensor, can be mounted flush with the wall in the container wall in the same manner as a port hole.

Expediently, relative to a pre-determined rest bed-dumping height of the respective product within the container, the microwave sensor is arranged at a height of approximately up to two times the rest bed-dumping height, preferably at the upper edge area of the rest bed within its rest bed-dumping height. On the one hand, the microwave sensor is thus arranged at a well-accessed position and, on the other hand, especially good measurement results arise with the arrangement at this height, because in this measurement position the fluidized bed is detected in a representative area.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
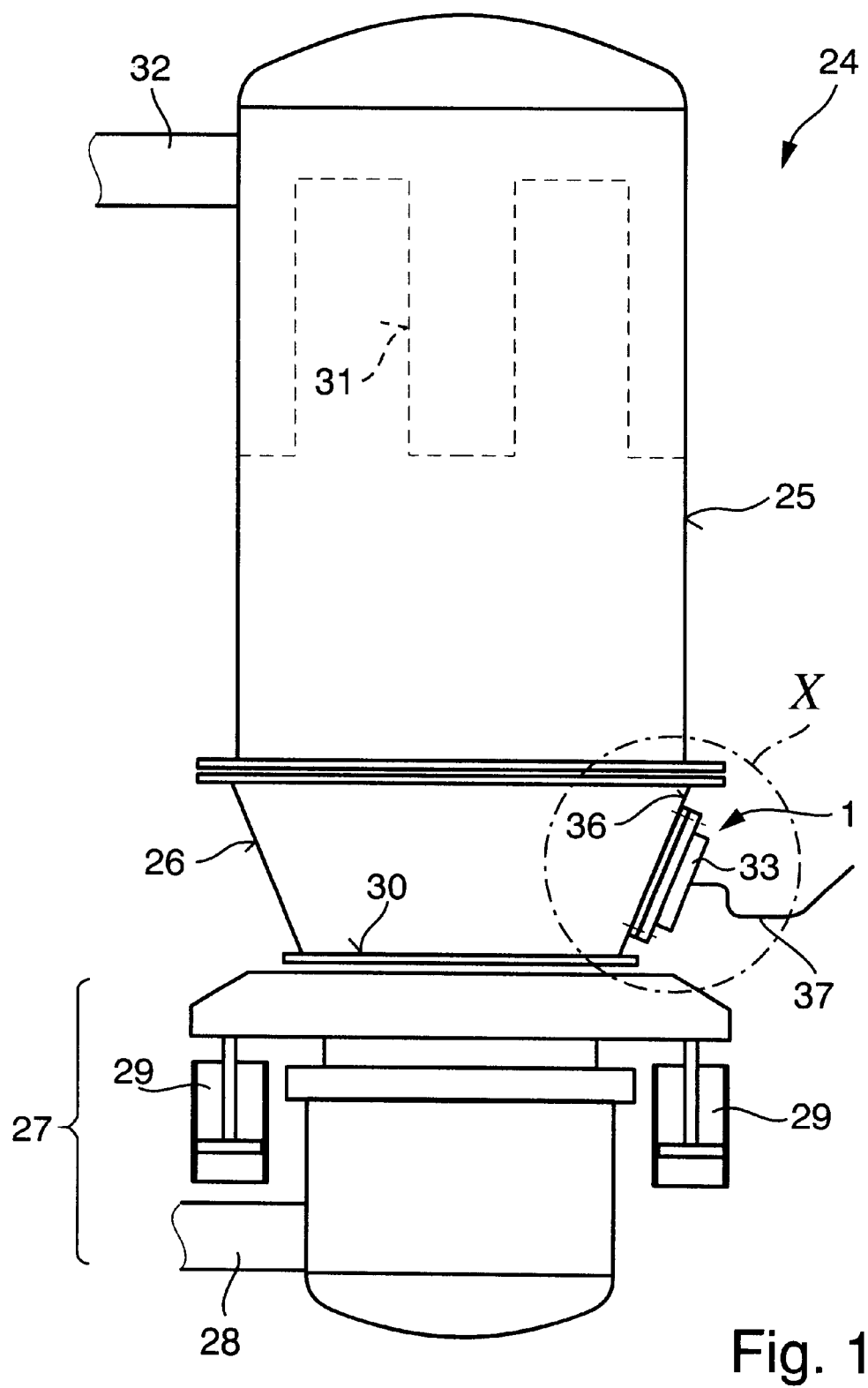
FIG. 1 is a side view of a fluidized layer apparatus with an impermeable seal as well as a microwave sensor.

FIG. 1 shows as an aeration device a fluidized layer apparatus 24, comprising essentially an upper part with a filter housing 25 as well as a material container 26 and a lower part 27, in which an air supply 28 is also located. On the lower part 27 a hydraulic cylinder 29 for closing the system can also be recognized, whereby the material container 26 is pressed against the filter housing 25. The air supplied in the air supply 28 reaches the material container 26 as well as the filter housing 25 via the lower part and a sieve bottom or blower stream bottom 30. With an appropriate air throughput, a fluidized bed forms in the material container and the filter housing from the material located in the container and to be treated. In the upper area of the filter housing 25 filters 31, indicated by dashed lines, are located, on whose clean gas side an exhaust conduit 32 is located.

Figure 2:
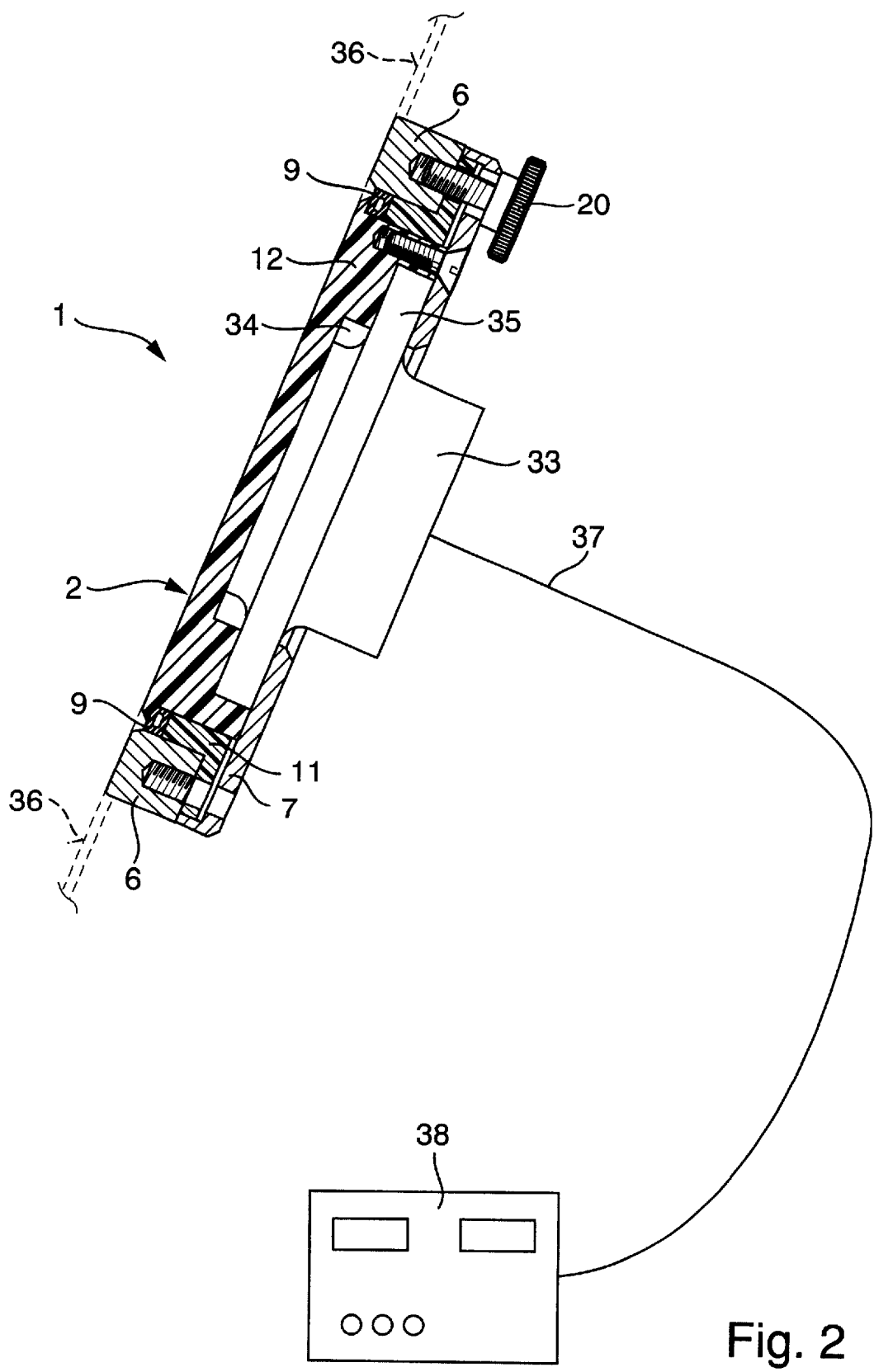
FIG. 2 is an enlarged sectional representation of the container wall according to the area "X" in FIG. 1, with an impermeable seal and a sensor.

On the material container 26 an impermeable seal is arranged, which has a carrier member 12 as part of a sensor holder. In the embodiment according to FIG. 2 the carrier member 12 is connected to a moisture sensor 33 constructed as a microwave sensor. In the embodiment according to FIG. 2 the carrier member 12 of the impermeable seal 1 has a recess opening 34, into which the moisture sensor 33 is inserted from the outside in. The sensor has an attachment flange 35 on which it is held by the detachable cover flange 7.

The carrier member 12 forms a protective cap for the sensor 33 and is closed tight with the container interior 36. It is also well recognized in FIG. 2 that the interior of the carrier member closes in an approximately flush manner with the container interior 36, i.e., seals in an essentially aligned or straight line manner with it. The container inner wall is thereby continued practically continuously, without any disruptive parts projecting into the container interior. With the microwave moisture sensor 33, another temperature sensor can be arranged. The sensor(s) are connected via electric cable 37 to an evaluation device 38, which can be part of a process control.

Using the moisture sensor, granulation, agglomeration, pelletizing, instantizing, coating and drying processes can be monitored in a fluidized layer or in a so-called single pot granulator. The product moisture represents an important process quantity. It functions for the monitoring, for example the maximum permissible product moisture, for a maintenance of a stable and homogeneous fluidization, or a suitably constant moisture for uniform granulation or as a measure for the end of the process during drying to a desired final moisture content. Using the microwave moisture sensor 33, an online product moisture measurement is possible, whereby, among other things, a higher spray rate is possible and thereby an increased throughput.

A suitable sensor can be constructed in the form of a planar sensor having a PTFE-seal, which can be assembled in a flush manner in the container wall of the fluidized layer apparatus, in the same manner as a port hole. This makes possible in a very simple way a retrofit to existing systems. Special sampling devices or covers are not necessary. The sensor can be easily integrated via standard flanges, such as are used also for port holes and spray nozzle mounts. From this, an essential advantage of the sensor results: owing to the difficult cleanability of large fluidized layer systems and the fact that in the pharmacy, partially highly active substances are processed, that are hazardous to health, it is important to clean the systems including their total accessory components as completely as possible, automatically and closed (Cleaning-In-Place or CIP cleaning). The system and the components used must have as few dead spaces as possible, and must be easy to clean. For this reason, all of the sensors which must be brought directly into the fluidized bed and which determine the product moisture via the diffusion of water vapor separate. The microwave sensor which measures in a contact-free manner can be sealed off via a special sealing system with the container wall having no dead spaces and can be completely cleaned by covering it with a TEFLON® cap without corners and edges, similar to a port hole.

In the measurement of the total product moisture using electromagnetic radiation in the high frequency range or microwave range, a certain penetration depth of the radiation into the fluidized layer is present and, as a function of the product moisture, a moisture-dependent resonance frequency and a corresponding attenuation of the radiation appear.

The moisture is measured via a sensor that operates in a high frequency range below 100 MHz or also in the microwave range. A suitable penetration depth is thereby achieved in the fluidized layer. The actual moisture of a particle is measured on the particle surface and inside the particle (important for granulation processes). The measurement signal is essentially only dependent on the moisture content of the particle and the product temperature. For example with high temperatures and low product moisture, a higher attenuation can result than with the same product moisture and a lower temperature. However, this effect can thereby be compensated in that at different temperatures (e.g., 20° C., 40° C., 60° C., and 80° C.) a calibration curve is established, which is correspondingly accessed during the measurement as a function of the measured product temperature. For this, a corresponding regulation can be developed.

On the other hand, during drying the effect of the temperature can be neglected, provided that only a 2-point calibration is performed (characterized initial moisture and desired end moisture), so that the signal measured at the end always detects the desired end value independently of the temperature. In contrast, during granulation an almost constant temperature (cooling boundary temperature) is to be taken into account. The effect of temperature can be neglected therein, and a calibration using several points is thereby possible, for example with five reference points.

A direct effect of the grain sizes in the range of 0.2 mm to 20 mm, typical for fluidized layer processes, is not to be expected. However, a variable grain size or a variable distribution thereof leads to a changed bulk density in the fluidized layer, which has an effect on the measurement signal. The effect of a variable density can, however, be compensated in the context of a suitable calibration and by a simultaneous detection of the resonance frequency and the attenuation.

The resonance frequency relates to the total fluidized layer or to parts thereof and not to an individual particle. Because of the good mixing in a fluidized layer, this total parameter is representative of the product moisture. A certain layer formation (typical for fluidized layers) on the sensor can be tolerated because of the penetration depth of the radiation within certain limits. This represents a significant difference from other processes. By the penetration depth of the electromagnetic radiation into the product, a distinction can be made during the process between a "moist granulation" and a "dry granulation."

In order to calibrate a measurement sensor operating with electromagnetic waves, a 2-point or multi-point, for example 5-point, calibration is possible in principle. Calibration is performed directly in the process system using real product and realistic process conditions, wherein these conditions must not yet have been optimized. A measurement curve is recorded during the process and plotted against an exact offline-reference (e.g., dry weight determination via scales). A correlation thereby results between the electronic measurement signal and the product moisture measured off-line. The product moistures then measured online during the actual process result on the basis of this calibration curve.

Upon scale-up one can orient oneself respectively to the already-determined calibration curve and check this in a first calibration process and, if necessary, re-define it. An additional calibration or statistical interpretation expenditure is not necessary.

To summarize in brief, the following essential advantages of the process result:

(a) higher spray rate and thereby an increased throughput;
(b) process convertable almost independently of the air supply conditions (well suited for scale-up);
(c) ideal transfer of laboratory-determined process to a processing system; and
(d) good cleanability in CIP-processes.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A method for monitoring and/or controlling and regulating a granulation, agglomeration, coating and/or drying process in a fluidized bed by determining the product moisture, the method comprising substantially continuously measuring a total product moisture during at least one process segment, in a contact-free manner using electromagnetic radiation in a high frequency or microwave range, by evaluation of attenuation of the radiation as a measure of the total product moisture, and taking into consideration the effect of the temperature of the product on the attenuation, holding the total product moisture in a predetermined range via a control circuit by changing at least one of granulation, agglomeration or coating moisture spray rate, gas temperature and volume flow.

2. The method according to claim 1, wherein via the measurement of the total product moisture in a granulation/coating process, a maximum permissible product moisture is determined for at least one of the following functions: maintaining a stable and homogeneous fluidization, regulating a pre-determined constant product moisture, and determining an end point of the granulation.

3. The method according to claim 1, wherein via the measurement of the total product moisture in a drying process, an endpoint of the process is determined by drying to a desired end moisture content.

4. The method according to claim 1, wherein via the measurement of the total product moisture in a granulation process, a reproducible grain size distribution correlating approximately with the total product moisture is maintained in a pre-determined range by changing at least one of the spray rate, the gas temperature, and the volume flow.

5. The method according to claim 1, wherein via the measurement of the total product moisture, a pre-determinable moisture progression is regulated via a direct correlation between the spray rate and the product moisture.

6. The method according to claim 1, wherein for a calibration in the context of a process adjusted to a laboratory standard and adaptation of the process based thereon to an actual production standard, an adjustment of the spray rate is performed using a measurement value of the total product moisture as an instrument-independent quantity.

* * * * *